United States Patent
De Lair et al.

(10) Patent No.: US 7,165,465 B2
(45) Date of Patent: Jan. 23, 2007

(54) DYNAMIC LOAD FIXTURE FOR APPLICATION OF TORSION LOADS FOR ROTARY MECHANICAL SYSTEMS

(75) Inventors: Charles M. De Lair, Pomerone, AZ (US); R. Brian Cline, Tucson, AZ (US); Christopher P. Owan, Tucson, AZ (US); Donald E. Croft, Tucson, AZ (US); Shane P. Stilson, Tucson, AZ (US)

(73) Assignee: Raytheon Company, Waltham, MA (US)

( * ) Notice: Subject to any disclaimer, the term of this patent is extended or adjusted under 35 U.S.C. 154(b) by 0 days.

(21) Appl. No.: 10/955,023

(22) Filed: Sep. 29, 2004

(65) Prior Publication Data

US 2006/0070457 A1 Apr. 6, 2006

(51) Int. Cl.
*G01L 3/02* (2006.01)
(52) U.S. Cl. .................................. 73/862.326
(58) Field of Classification Search ................ 73/847, 73/862.325–862.326, 865.9
See application file for complete search history.

(56) References Cited

U.S. PATENT DOCUMENTS 3,712,127 A * 1/1973 Petersen ................... 73/118.1
3,754,437 A * 8/1973 Kanbel et al. .............. 73/811
4,414,854 A * 11/1983 Haeg ........................ 73/847
4,807,467 A * 2/1989 Kugler ..................... 73/118.1
6,591,200 B1 * 7/2003 Cohen et al. ............... 702/38
6,988,420 B2 * 1/2006 Peterson et al. ......... 73/862.31
2004/0135534 A1 * 7/2004 Cullen ...................... 318/609
2004/0255698 A1 * 12/2004 Beaman et al. ......... 73/862.49

* cited by examiner

*Primary Examiner*—Max Noori
(74) *Attorney, Agent, or Firm*—Horace St. Julian; Leonard A. Alkov; Karl A. Vick (57) ABSTRACT

A dynamic load fixture (DLF) applies a torsion load to a unit under test (UUT) to achieve the demanding aerodynamic load exposures encountered by a control actuation system (CAS) in flight. Instead of fixing the end of the torsion bar, the DLF controls the application of torque to the torsion bar, hence the UUT via a DLF motor. The dynamic load can be independent of the angular rotation of the UUT, which allows the DLF to more effectively reproduce desired acceptance tests such as torque-at-rate and nonlinear loads. Furthermore, application of the loads through a torsion bar allows the system the compliance needed to generate precise loads while allowing for the flexibility of changing torsion bars to test a wide variety of UUT on one test platform. To achieve the demanding aerodynamic load exposures encountered by a CAS in flight, the controller must be able to respond both very fast and very precisely. Control is enhanced by the thorough characterization of the DLF and application of either "classic" negative feedback control or "modern" state-space control methods of linear observers and quadratic optimum control.

27 Claims, 7 Drawing Sheets

DYNAMIC LOAD FIXTURE FOR APPLICATION OF TORSION LOADS FOR ROTARY MECHANICAL SYSTEMS

BACKGROUND OF THE INVENTION

1. Field of the Invention

This invention relates to test fixtures for applying loads to a rotary mechanical system and more specifically to dynamic load fixtures for applying a controllable torsion load capable of replicating acceptance test procedures and nonlinear load conditions.

2. Description of the Related Art

The use of rotary mechanical systems to power automobiles, drive robotics, actuate flight control systems on airplanes and missiles and many other mechanical systems is ubiquitous throughout our economy. The use of a motor to rotate a shaft to actuate these various systems is a cost effective and reliable way to convert electrical energy into a mechanical force. In many applications such as found in an automobile, the motor rotates the drive shaft at a high and relatively constant rate. Therefore, the shaft has a large range of motion but a relatively small frequency content. In other applications such as found in an airplane, the motor rotates the drive shaft over a small range of motion, less than ten turns or even a single turn, to actuate flight control. In applications such as found in a missile, the motor rotates the drive shaft over a small range of motion but at a very high rate to control the deployment of the fins, canards or wings to guide the missile.

The different applications and environments produce a wide range of load conditions for the rotary mechanical systems. Before a design can be approved or, in some cases, a particular system fielded, it must be tested to determine how the system performs under certain load conditions. More specifically, when a torque is applied to the shaft how does the system respond?

Figure 1:
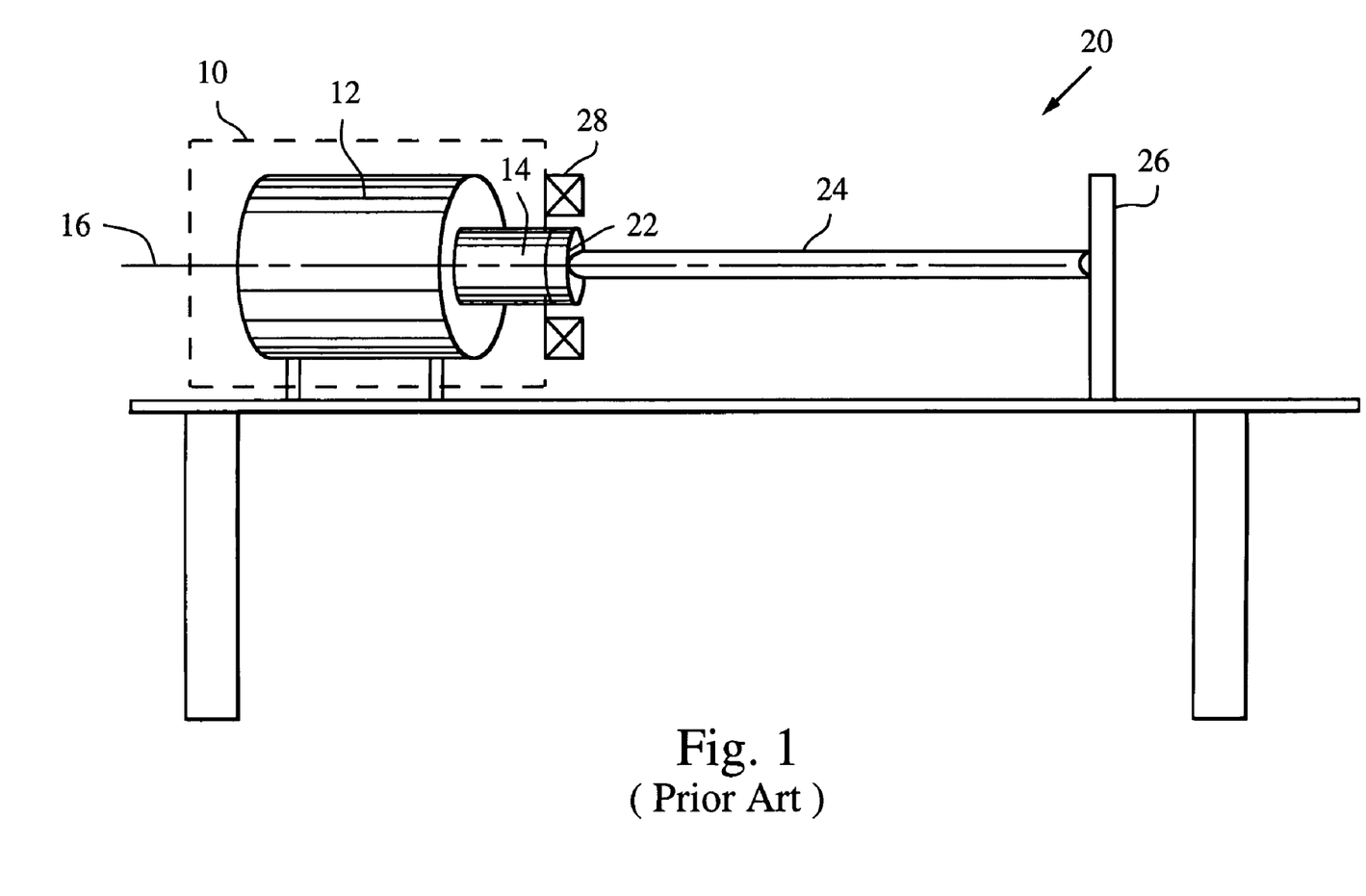
FIG. 1, as described above, is a schematic diagram of a known test fixture for applying a torsion load to a rotary mechanical system.

Conventional techniques for testing control actuation systems (CAS) used for steering control of guided missiles and flight vehicles typically employ fixed end torsion bars to simulate aerodyanic loads encountered in flight. As shown in FIG. 1, a CAS 10, referred to as a unit under test (UUT) during testing, includes an actuator device 12 and a drive shaft 14 that rotates about an axis 16. A conventional test fixture 20 includes an interface bracket 22 that is bolted to the end of drive shaft 14, a torsion bar 24 that is rigidly mounted on the interface bracket along axis 16, and a plate 26 that fixes the other end of the torsion bar to a mechanical ground. A measuring device 28 is placed around the interface bracket to measure the angular rotation of the torsion bar when the unit under test is activated. The amount of torque in the torsion bar, hence the load applied to the UUT is proportional to the angle of rotation.

This approach limits the evaluation to quasi-static conditions at small deflection changes and prohibits testing of the CAS under desired acceptance test procedures and realistic load environments demanded of typical flight scenarios. Specifically, a "torque at rate" test procedure requires the application of a constant torque load for a constant rotation rate of the drive shaft. Typical flight scenarios produce rapidly changing nonlinear load conditions. Clearly a fixed end torsion bar cannot replicate these conditions. Furthermore, to test the UUT over a range of load conditions albeit quasi-static an operator must replace the torsion bar with a different torsion bar having different stiffness properties. This is very inconvenient and slow.

SUMMARY OF THE INVENTION

The present invention provides a dynamic load fixture (DLF) for applying a dynamic torsion load to a rotary mechanical system to achieve the demanding aerodynamic load exposures encountered by a CAS in flight. Real-time control of a dynamic load that can be independent of the angular rotation of the CAS unit under test (UUT) allows the DLF to more effectively reproduce desired acceptance tests such as torque-at-rate and real life conditions via nonlinear loads with a high response bandwidth. The DLF is particularly well suited for rotary mechanical systems that exhibit a limited range of motion and high frequency content such as control actuation systems (CAS) used for steering control of guided missiles and flight vehicles.

The DLF comprises a torsion bar that is mechanically coupled to the rotating shaft of a UUT along an axis of rotation. A DLF motor applies torque to the torsion bar to apply a load to the shaft. Sensors measure the angular rotation of and the torque applied to the UUT shaft. Based on the measurement data, models of the DLF and in some cases the UUT, and the load command $U_{DLF}(s)$ a controller generates a command signal $C(s)$ to the motor to adjust the application of torque to the torsion bar so that the actual measured load closely approximates the load command. The combination of the DLF motor and torsion bar provides the necessary compliance to generate precise loads, the flexibility to test a wide variety of UUTs, and the ability to perform torque-at-rate and nonlinear load tests.

To achieve the demanding aerodynamic load exposures encountered by a CAS in flight, the controller must be able to respond both very fast and very precisely. Conventional servo controllers such as PID feedback although adequate for certain test conditions do not provide optimum response. Control is enhanced by the thorough characterization of the DLF and application of either "classic" negative feedback control or "modern" state-space control methods of linear observers and quadratic optimum control. In addition, the UUT itself can be characterized and modeled and incorporated either in a separate feed forward control with phase lead compensation ("classic") or in the state-space controller with the UUT states included in the characteristic equations. This allows the controller to anticipate and thereby correct for the response of the UUT to an applied torque, which in turn greatly enhances the effective bandwidth of the controller.

A classic controller suitably comprises a feed forward controller $G_{FF}$ and a phase lead controller $G_C$. The feed forward controller is used to anticipate and correct any errors in the load caused by the properties of the UUT. The position command $U_{UUT}(s)$ sent to the UUT is also input to the feed forward controller, which based on a priori knowledge of a specific UUT, generates a correction to the load command $U_{DLF}(s)$. The phase lead controller $G_C$ generates a DLF motor command signal by passing the input through a filter.

A modern controller suitably comprises a state space controller $G_{SS}$ that includes a state estimator and a linear quadratic optimizer (LQO). Typically it is not possible to measure all of the states of the system that are important for control. The state estimator estimates the unmeasured state variables by using the states that are capable of being measured, the commands being sent to the DLF motor, the model of the DLF, and in some cases a model of the UUT. With all of the state variables either measured or estimated, the LQO optimizes the placement of the closed loop poles of the system based on the desired performance, saturation limits such as current, and the open loop poles of the system. The optimized estimate is subtracted from the load command $U_{DLF}(s)$ to generate the command signal C(s).

In one embodiment, the state space controller $G_{SS}$ models only the motor and torsion bar and receives as inputs the load command $U_{DLF}(s)$ and the measured angular rotations O(s) as a measure of both the position of the UUT and the dynamic load. In this implementation the controller is independent of the UUT.

In another embodiment, the state space controller $G_{SS}$ models both the DLF and the UUT. The state space controller receives as inputs the load command $U_{DLF}(s)$, the measured angular rotations O(s) and the position command $U_{UUT}(s)$. Incorporation of both the DLF and UUT models in the state space controller is more complex than separate state space and feed forward controllers. However, performance should improve because actual measurements are used in conjunction with the UUT model.

These and other features and advantages of the invention will be apparent to those skilled in the art from the following detailed description of preferred embodiments, taken together with the accompanying drawings, in which:

DETAILED DESCRIPTION OF THE INVENTION

The present invention provides a dynamic load fixture (DLF) for applying a dynamic torsion load to a rotary mechanical system to achieve the demanding aerodynamic load exposures encountered by a control actuation system (CAS) in flight. Instead of fixing the end of the torsion bar, the DLF controls the application of torque to the torsion bar, hence the UUT via a DLF motor. Consequently the dynamic load can be independent of the angular rotation of the CAS unit under test (UUT), which allows the DLF to more effectively reproduce desired acceptance tests such as torque-at-rate and nonlinear loads. To provide the high response bandwidth needed to effectively test the UUT, the DLF employs classical phase lead or modern state space control, which is suitably augmented with a priori characterization information of the UUT. The DLF is particularly well suited for rotary mechanical systems that exhibit a limited range of motion and high frequency content such as control actuation systems (CAS) used for steering control of guided missiles and flight vehicles.

Figure 2A:
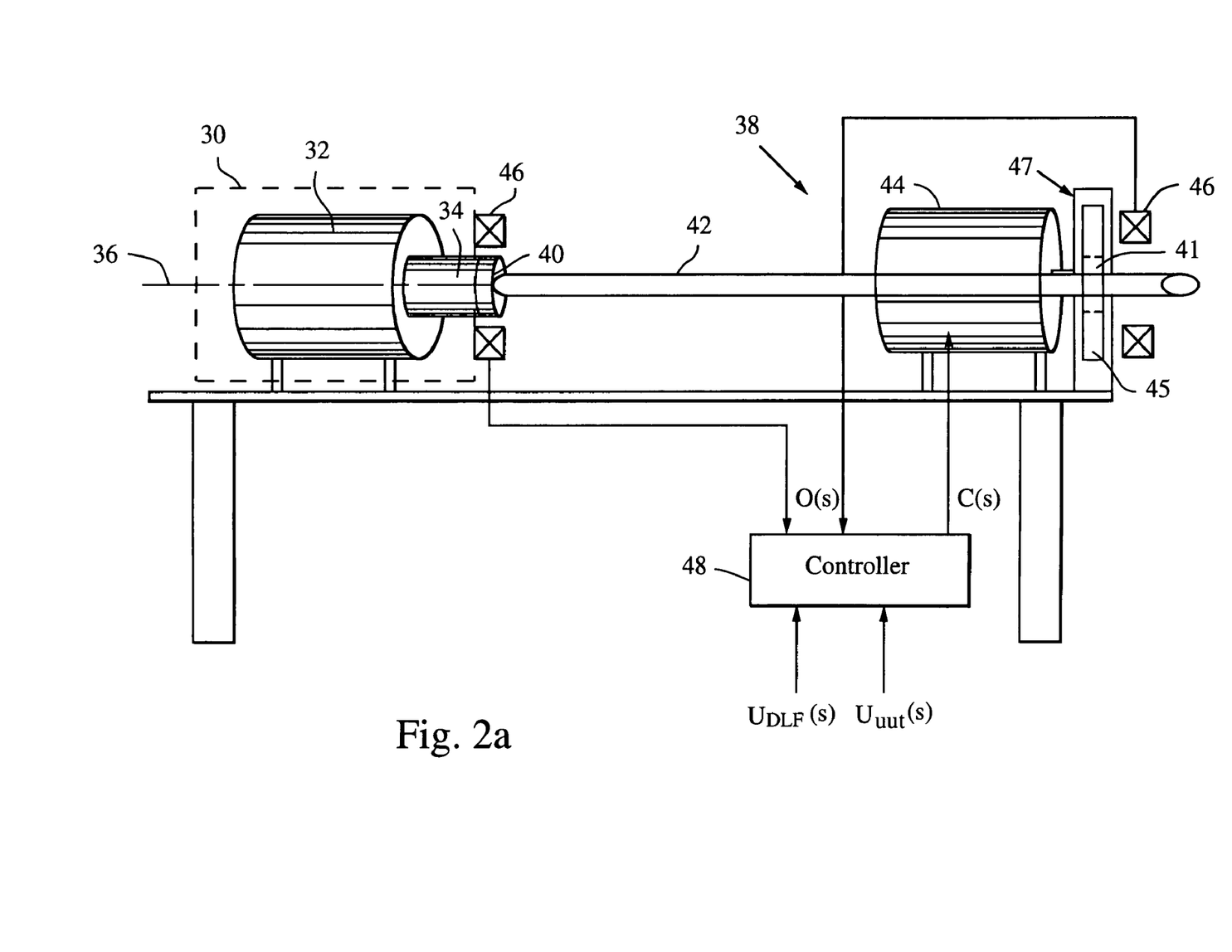
FIGS. 2a and 2b are side and top views of a simplified block diagram of a dynamic load fixture (DLF) for applying a dynamic load to a rotary mechanical system in accordance with the present invention.
Figure 2B:
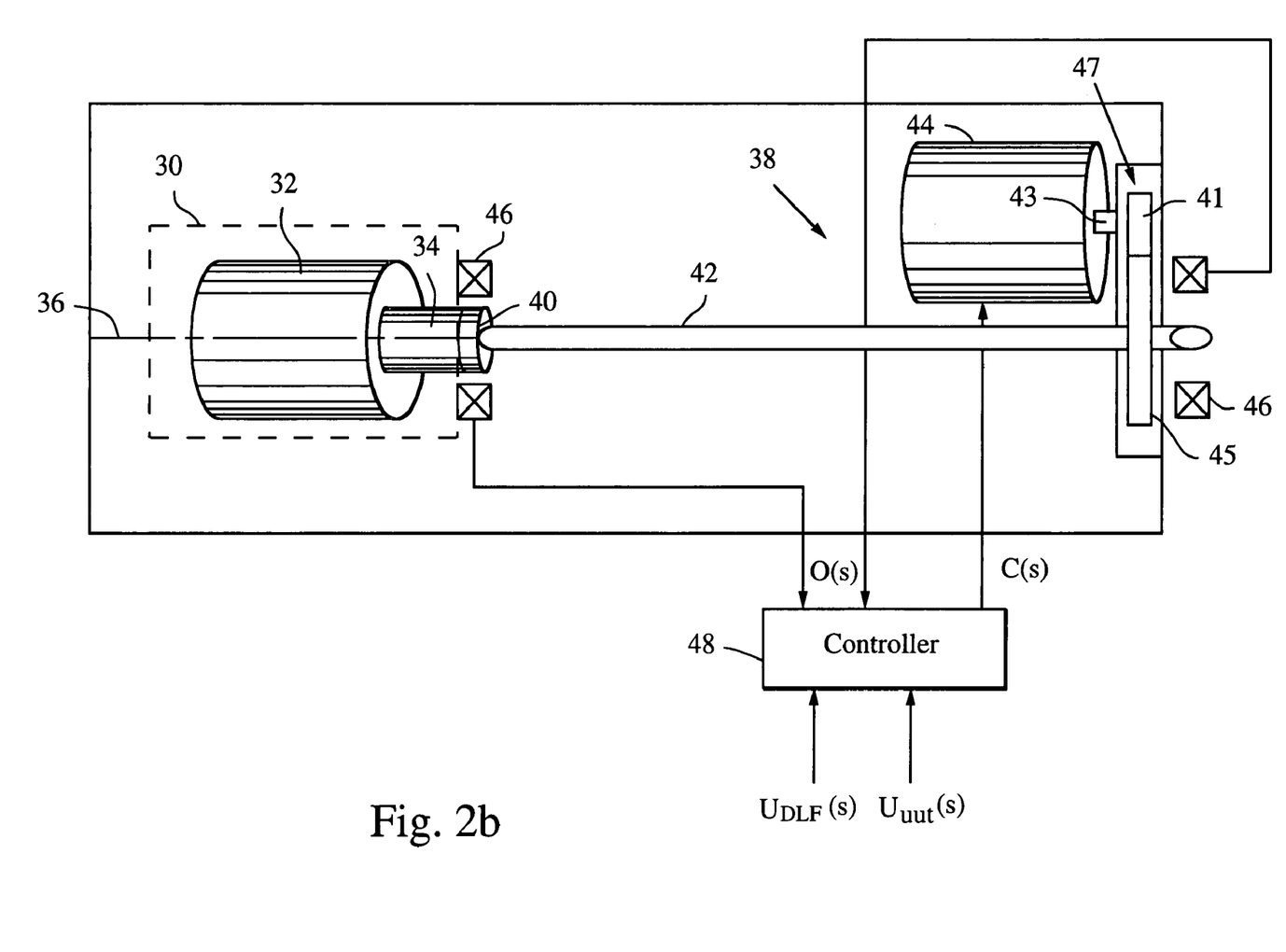

As shown in FIG. 2, a CAS 30, referred to as a unit under test (UUT) during testing, includes a motor 32 and a drive shaft 34 that rotates about an axis 36. A DLF 38 comprises an interface bracket 40 that is secured to the end of drive shaft 34 and a torsion bar 42 that is rigidly mounted on the interface bracket along axis 36. A DLF motor 44 applies torque to the torsion bar 42 to apply a dynamic load (torque) to drive shaft 34. The current embodiment of the DLF uses a gear train in order to increase the maximum torque applied by the specific motor used to a specific torque range of UUT. The gear train uses a pinion spur gear 41 on the motor output shaft 43 interfacing to an output spur gear 45 attached to the torsion bar shaft 42. The pinion and output gears are mounted in a gear box 47. Depending on the DLF motor used and the UUT to be tested a gear train may not be required to produce the desired results. Given that the motor can produce the necessary torque, the motor 44 can be attached directly to the torsion bar 42.

Sensors 46 measure the angular rotation of and the torque applied to the drive shaft 34. One sensor is typically placed at the interface bracket and the other sensor is suitably placed near the motor. Based on the measurement data O(s), models of the DLF, the load command $U_{DLF}(s)$, and in some cases a model of the UUT and the position command $U_{UUT}(s)$, a controller 48 generates a command signal C(s) to the DLF motor 44 to adjust the application of torque to the torsion bar 42 so that the actual measured load closely approximates the load command $U_{DLF}(s)$. The load command $U_{DLF}(s)$ represents the ideal load applied to the UUT at an instant in time and the position command $U_{UUT}(s)$ represents the position the UUT is trying to go at an instant in time. By designing a feedback controller based on the dynamic response of the system the load actually applied to the UUT can closely approximate the load command sent to the DLF. As will be discussed in more detail in the following paragraph, the "system" on which the feedback controller is developed can be the DLF or a combination of the UUT and DLF.

Figure 3:
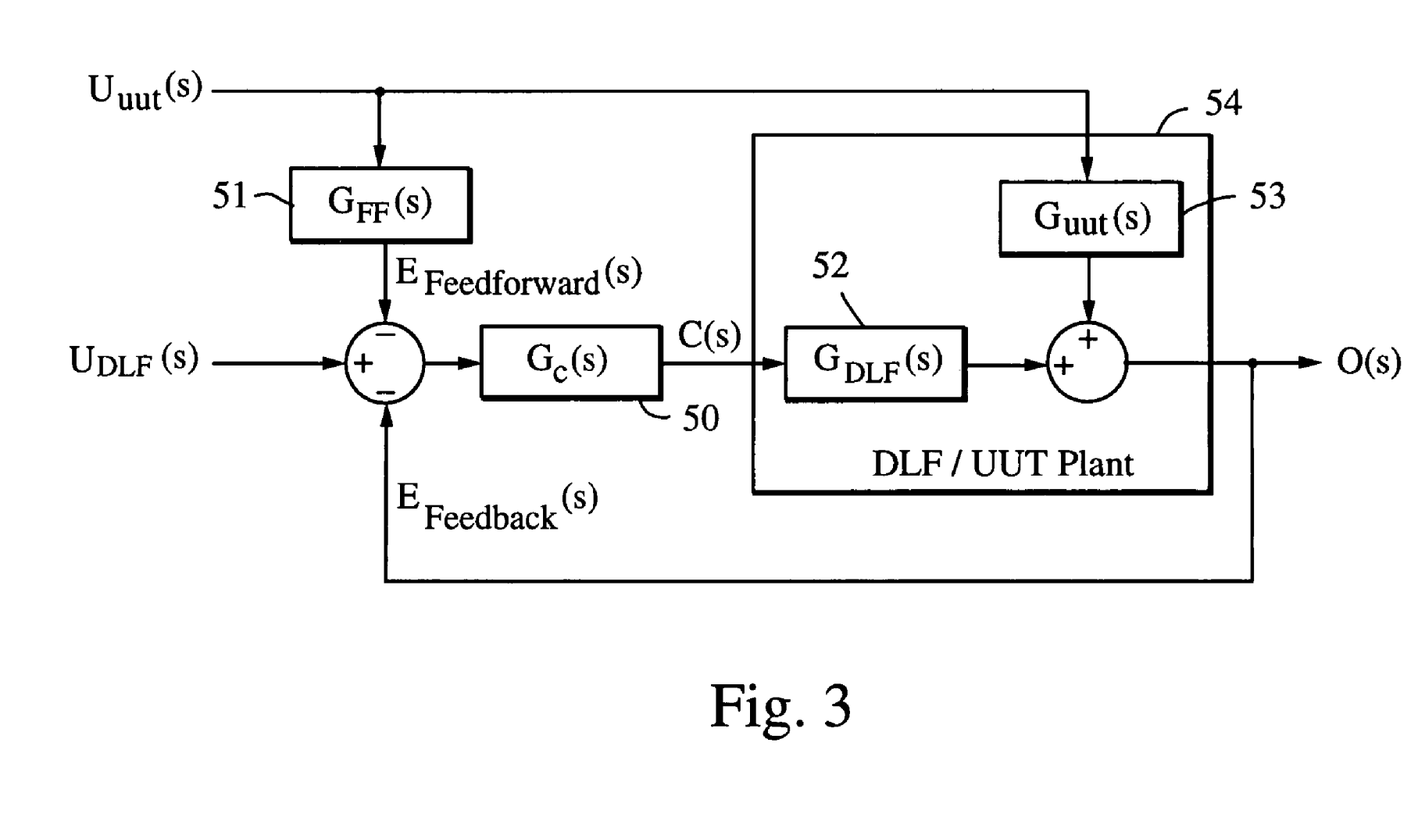
FIG. 3 is a block diagram of a classic controller including a separate feed forward control $G_{FF}$ with phase lead compensation.
Figure 4:
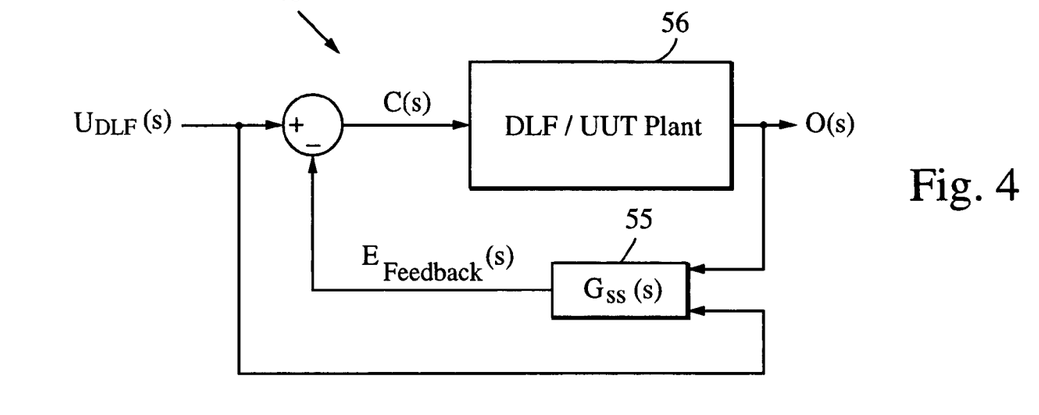
FIG. 4 is a block diagram of a modern controller including a state space controller $G_{SS}$.
Figure 5:
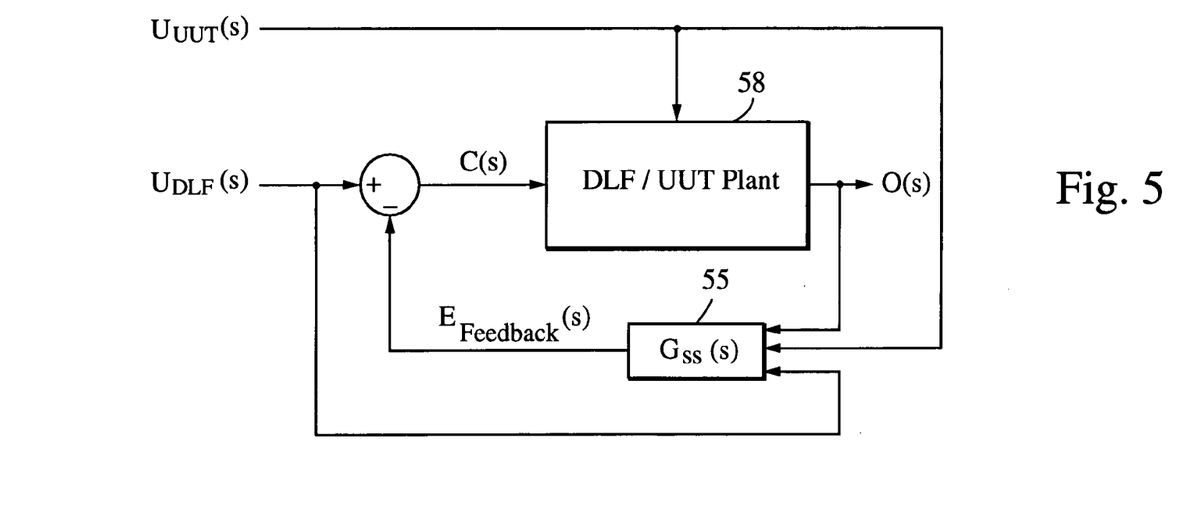
FIG. 5 is a block diagram of the modern state space controller $G_{SS}$ in which the response to the UUT command is incorporated into the state space controller $G_{SS}$.

To achieve the demanding aerodynamic load exposures encountered by a CAS in flight, the controller 48 must be able to respond both very fast and very precisely. Conventional servo controllers such as PID feedback although adequate for certain test conditions do not provide optimum response. Control is enhanced by the thorough characterization of the DLF and application of either "classic" negative feedback control or "modern" state-space control methods of linear observers and quadratic optimum control. In addition, the UUT itself can be characterized and modeled and incorporated either in separate feed forward control $G_{FF}$ with phase lead compensation ("classic") or the state-space control $G_{SS}$ with the UUT states included in the characteristic equations ("modern"). This allows the controller to anticipate and thereby correct for the response of the UUT to an applied torque, which in turn greatly enhances the effective bandwidth of the controller 48. FIGS. 3 through 5 illustrate how both classic and modern controllers interact with the physical system of the DLF and UUT, i.e. the "plant".

As shown in FIG. 3, a controller 48 based on classic control theory includes a phase lead controller $G_C$ 50 and a feed forward controller $G_{FF}$ 51. The feed forward controller 51 is used to anticipate and correct any errors in the load caused by the properties of the UUT. A position command $U_{UUT}(s)$ is input to the feed forward controller, which based on a priori knowledge of a specific UUT, generates a correction $E_{Feedforward}(s)$ to the load command $U_{DLF}(s)$. The feed forward controller $G_{FF}$ is chosen such that the numerator of the transfer function shown in equation (1), with $U_{UUT}(s)$ as the input and $O(s)$ as the output, is as close to zero as possible. If this numerator is equal to zero complete rejection of the error generated by the UUT on the DLF will be achieved. This is achieved by setting $G_{ff}$ using equations (3). $G_C$ is determined using equation (2) and $G_{DLF}$ 52 and $G_{UUT}$ 53 are mathematical representations of the system described in equations 4–10. In this feed forward configuration, the phase lead controller $G_C$ 50 receives as input the load command $U_{DLF}(s)$ minus $E_{Feedforward}(s)$ and $E_{Feedback}$ ($O(s)$ from the DLF/UUT plant 54 (UUT 30, torsion bar 42 and motor 44)), as a measure of both the position of the UUT and the dynamic load. The phase lead controller $G_C$ generates a DLF motor command signal $C(s)$ by passing the input through the filter as described in equation (2), where $a_1$, $a_0$ and $b_1$ are chosen to achieve the desired response.

$$\text{Feed\_Forward\_Control} = \frac{G_{uut}(s) - G_{FF}(s) G_C G_{DLF}(s)}{1 + G_C G_{DLF}(s)} \quad (1)$$

$$G_C = \frac{a_1 s + a_0}{b_1 s + 1} \quad (2)$$

$$G_{FF} = \frac{G_{uut}}{G_{DLF} G_C} \quad (3)$$

As shown in FIGS. 4 and 5, a controller 48 based on modern control theory comprises a state space controller $G_{SS}$ 55 that can be implemented in a number of configurations. As shown in FIG. 4, the state space controller $G_{SS}$ 55 models only the DLF part of the DLF/UUT Plant 56 (torsion bar 42 and motor 44) and receives as inputs the load command $U_{DLF}(s)$ and the measured angular rotations $O(s)$ from the DLF plant 56 as a measure of both the position of the UUT and the dynamic load. The angular rotations and the physical characteristics of the torsion bar determine the load applied to the UUT. In this implementation the controller is independent of the UUT. The state space controller $G_{SS}$ generates an estimate of the states and applies gains to these in order to place the closed loop poles of the system in locations that will produce the desired response. The states of the system can be all or a subset of the following; motor current, motor position and velocity, pinion gear position and velocity, output gear position and velocity, and load position and velocity. The states, multiplied by the predetermined gains, are summed to create the feedback signal $E_{Feedback}(s)$, which is subtracted from the load command $U_{DLF}(S)$ to generate the command signal $C(s)$ to drive the DLF motor 44.

As shown in FIG. 5, the state space controller $G_{SS}$ 55 models both the DLF 38 and the UUT 30. The state space controller 55 receives as inputs the load command $U_{DLF}$, the measured angular rotations $O(s)$ from the DLF/UUT plant 58 and the position command $U_{UUT}(s)$. Incorporation of both the DLF and UUT models in the state space controller is more complex than separate state space and feed forward controllers. However, performance should improve because actual measurements $O(s)$ are used in conjunction with the UUT model.

Figure 6:
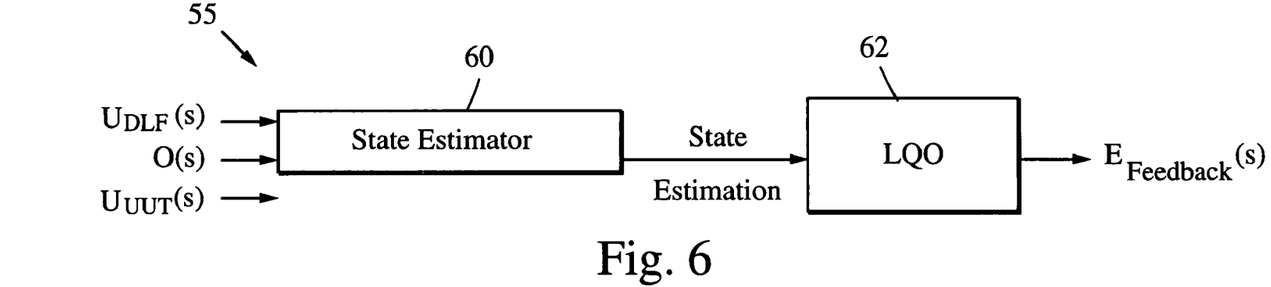
FIG. 6 is a block diagram of the state space controller $G_{SS}$.

As shown in FIG. 6, the state space controller $G_{SS}$ 55 comprises a state estimator (SE) 60 and a linear quadratic optimizer (LQO) 62. Typically it is not possible or practical to measure all of the states of the system that are important for control. The state estimator 60 estimates the unmeasured state variables by using the states that are capable of being measured $O(s)$, the commands being sent to the DLF motor $U_{DLF}(s)$ and the model of the DLF. In the embodiment shown in FIG. 5, the state estimator also uses a model of the UUT and the position command $U_{UUT}(s)$. With all of the state variables either measured or estimated, the LQO 62 optimizes the placement of the closed loop poles of the system based on the desired performance, saturation limits such as current, and the open loop poles of the system. The optimized estimate $E_{Feedback}(s)$ is subtracted from the load command $U_{DLF}(s)$ to generate the command signal $C(s)$ to drive the DLF motor 44.

Figure 7:
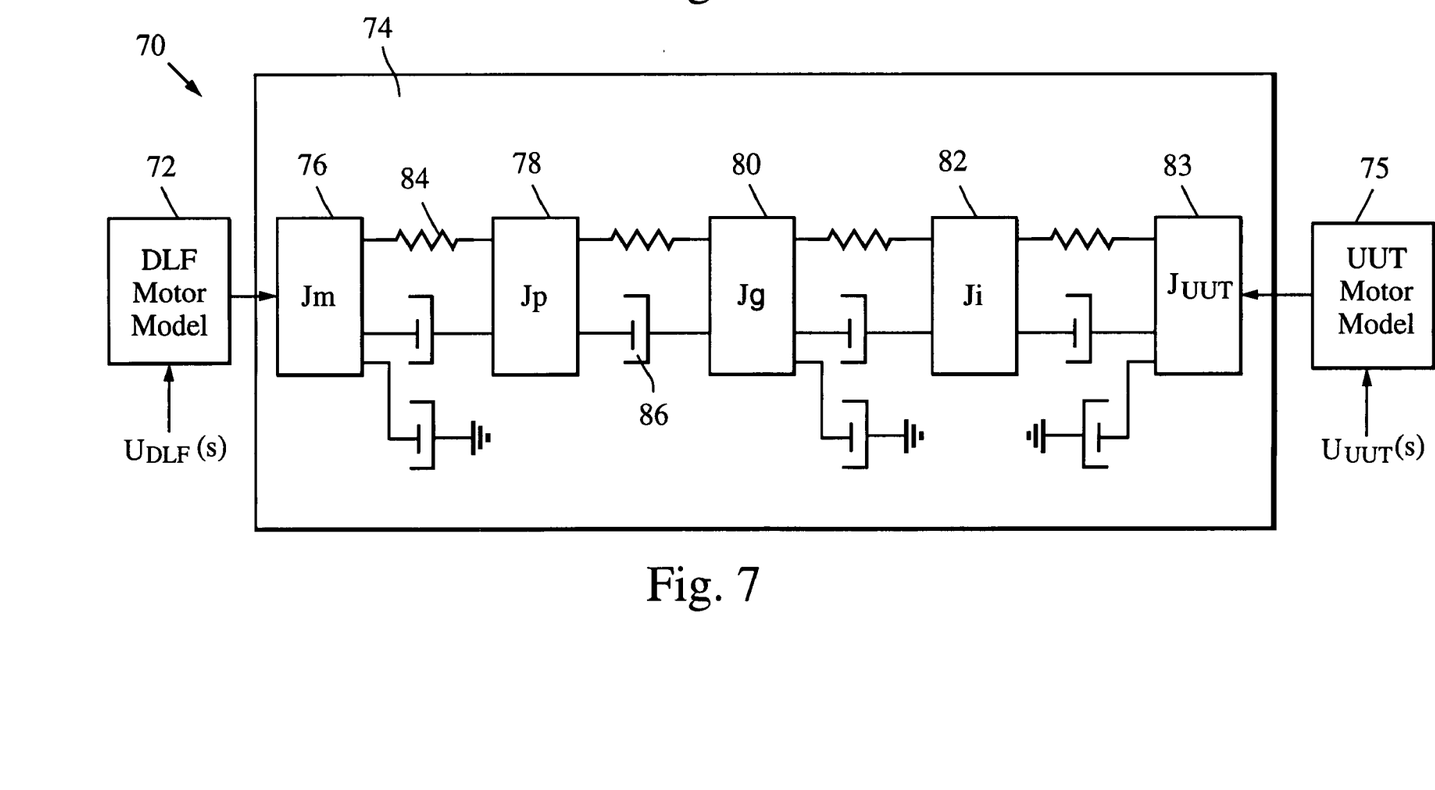
FIG. 7 is a schematic diagram of an nth order model of the dynamic load for which a reduced nth order state estimator can be developed.

To implement the state space controller $G_{SS}$ the DLF must first be characterized and modeled. As shown in FIG. 7, a model 70 of the DLF includes an electrical DLF motor model 72, a mechanical model 74, and an electrical and mechanical UUT motor model 75. The $9^{th}$ order mechanical model comprises the DLF motor, pinion, gear, load and UUT masses 76, 78, 80, 82 and 83, respectively, system springs 84 and system dampening elements 86. Lower order models can be formulated by lumping some of the parameters together.

The $G_{SS}$ used in the configuration shown in FIG. 5 also incorporates a model of the UUT. The model of the DLF produces the previously mentioned states of motor current, motor position and velocity, pinion position and velocity, gear output position and velocity and load position and velocity. Including the UUT in $G_{SS}$ adds additional states which deal with the dynamics of the UUT. At a minimum the UUT states of UUT motor current, UUT output position and velocity are added to the DLF states in $G_{SS}$. The equations and number of states developed for the UUT will be dependant on the UUT specific design and complexity. $G_{UUT}$ shown in equation (10) will vary depending on the UUT and can have a significant impact on equation (10). It is not intended to provide a comprehensive representation for the all UUT here, but to show a place holder for the technique that would be employed for this embodiment.

To form the state estimator 60 for the configuration shown in FIG. 5, the motor model 72 and $9^{th}$ order DLF mechanical model 74 are interpreted mathematically to formulate a series of 1st order differential equations that represent the electrical and mechanical systems of the actual physical DLF/UUT plant between the command signal $C(s)$ and the measured data $O(s)$. In this system of equations, equation 4 represents electrical motor response, equations 5–8 represent the mechanical motor, pinion, gear and load response of the DLF, equation 9 the mechanical interaction of the UUT and DLF and equation 10 the UUT electrical motor, as follows:

$$\dot{I} = -\left[\frac{K_{fb}K_{fg} + R_m}{L_m}\right]I - \left[\frac{K_{bmf}}{L_m}\right]\dot{\theta}_m + \left[\frac{K_{fg}}{L_m}\right]I_{cmd} \quad (4)$$

$$\ddot{\theta}_m = -\left[\frac{K_p}{J_m}\right]\theta_m - \left[\frac{B_m + B_p}{J_m}\right]\dot{\theta}_m + \left[\frac{K_p}{J_m}\right]\theta_p + \left[\frac{B_p}{J_m}\right]\dot{\theta}_p + \left[\frac{T}{J_m}\right] \quad (5)$$

$$\ddot{\theta}_g = \left[\frac{K_g}{J_g Gr}\right]\theta_p + \left[\frac{B_{g1}}{J_g Gr}\right]\dot{\theta}_p - \left[\frac{K_g + K_L}{J_g} + \right]\theta_g - \left[\frac{B_{g1} + B_{g2} + B_L}{J_g}\right]\dot{\theta}_g + \left[\frac{K_L}{J_g}\right]\theta_L + \left[\frac{B_L}{J_g}\right]\dot{\theta}_L \quad (6)$$

$$\ddot{\theta}_p = \left[\frac{K_p}{J_p}\right]\theta_m + \left[\frac{B_p}{J_p}\right]\dot{\theta}_p - \left[\frac{K_p + \frac{K_g}{Gr^2}}{J_p}\right]\theta_p - \left[\frac{B_p + \frac{B_{g2}}{Gr^2}}{J_p}\right]\dot{\theta}_p + \left[\frac{K_g}{J_pGr}\right]\theta_g + \left[\frac{B_{g1}}{J_pGr}\right]\dot{\theta}_g \quad (7)$$

$$\ddot{\theta}_L = \left[\frac{K_L}{J_L}\right]\theta_g + \left[\frac{B_L}{J_L}\right]\dot{\theta}_g - \left[\frac{K_L + K_{bar}}{J_L}\right]\theta_L - \left[\frac{B_L + B_u}{J_L}\right]\dot{\theta}_L + \left[\frac{K_{Bar}}{J_L}\right]\theta_u + \left[\frac{B_u}{J_L}\right]\dot{\theta}_u \quad (8)$$

$$\ddot{\theta}_u = \left[\frac{K_{Bar}}{J_{uut}GR_{uut}^2}\right]\theta_L - \left[\frac{B_u}{J_{uut}GR_{uut}^2}\right]\dot{\theta}_L - \left[\frac{K_{Bar}}{J_{uut}GR_{uut}^2} +\right]\theta_u - \left[\frac{B_u}{J_{uut}GR_{uut}^2} + \frac{B_{uut}}{J_{uut}}\right]\dot{\theta}_u + \left[\frac{K_{Tuut}}{J_{uut}GR_{uut}}\right]I_{uut} \quad (9)$$

$$\dot{I}_{uut} = \left[\frac{G_{uut}}{L_{muut}}\right]U_{uut} - \left[\frac{G_{uut}GR_{uut}}{L_{muut}}\right]\theta_u - \left[\frac{K_{ubmf}GR_{uut}}{L_{muut}}\right]\dot{\theta}_u - \left[\frac{R_{muut}}{L_{muut}}\right]I_{uut} \quad (10)$$

where,
$J_m$=Motor Mass
$J_p$=Pinion Gear Mass
$J_g$=Output Gear Mass
$J_i$=Output Mass
$K_p$=Motor to Pinion Stiffness
$K_g$=Pinion to Gear Stiffness
$K_i$=Gear to Load Stiffness
$K_{bar}$=Torsion Bar Stiffness
$J_{uut}$=UUT Inertia Buut=UUT Damping
$GR_{uut}$=UUT Gear Ratio
$B_m$=Motor Damping
$B_p$=Motor to Pinion Damping
$B_{g1}$=Pinion to Gear Damping
$B_{g2}$=Gear Damping
$B_i$=Gear to Load Damping
Gr=Gear Ratio
$L_m$=Motor Inductance
$B_u$=Load to UUT Damping
$B_{uut}$=UUT Damping These equations are put into the state space form shown in Equations 11 and 12 as follows:

$$\dot{x} = Ax + Bu \quad (11)$$

$$y = Cx + Du \quad (12)$$

where,
x=state vector
A=square constant matrix
u=input vector
D=constant matrix
y=output vector
B=constant matrix
C=output vector
=derivative operator These equations are an example of baseline model for a 9$^{th}$ order mechanical model used to simulate the system and to develop the state space control techniques described herein. The same equations can be simplified for the state-space controller shown in FIG. 4 by removing the UUT portions and can be used to develop the transfer function for the classic controller shown in FIG. 3.

If possible, it is desired to measure and use for feedback all of the states of the system. However, typically one is not able to measure all of the states that are important for control. For those that can not be measured it is possible to develop an observer to estimate these state variables. This observer estimates the unmeasured state variables by using the states that are capable of being measured and the commands being sent to the plant. For example, in a current DLF the output gear position and UUT position states may be measured and the remaining states may be estimated. The state estimator shown in Equation 13 allows for the placement of poles in desired locations.

$$\dot{\hat{x}} = A\hat{x} + Bu + K(y - C\hat{x}) \quad (13)$$

where K=gain matrix and $\hat{x}$=estimated states vector.

The estimator pole locations for this application were chosen such that all poles are stable and as fast as or faster than the open loop poles of the system. Having placed the closed loop poles of the system using a linear observer, optimization can be applied to conduct trades on the system to maximize performance with out adverse effects resulting from the power limits existing in a physical system.

Linear, Quadratic Optimal Control provides an efficient method to optimize the way in which the control law gains are chosen. Equation 14 shows two important matrices in this method, Q and R.

$$V = \int_t^T [x'(\tau)Q(\tau)x(\tau) + u'(\tau)Ru(\tau)]d\tau \quad (14)$$

where,
Q=State Weighting Matrix
x=States
t=Present Time
R=Control Weighting Matrix
u=Inputs
T=Terminal Time By choosing values for these matrixes, which correspond to desired performance, the cost function shown in Equation 14 can be minimized. The weightings that are chosen for Q determine the importance of the states themselves and the importance of the states in how they relate to one another. For this particular application the output position and velocity of the system are most important and are weighted accordingly in the Q matrix. Weighting of R serves to limit the control input variable u. In pursuit of the best system response possible it may occur that the power available to the system will become saturated. It is typically desired to operate as close to the system saturation limits as possible without exceeding them too often. If they are exceeded too often the system will cease to behave as would be predicted by the linear system described by Equations 11 and 12, and performance is lost. Weighting of R allows for the trading of performance of the system against physical system limitations. Having Q and R set allows for the minimization of the cost function resulting in optimal gains for the G matrix in Equation 15 and final placement of the closed loop poles of the system.

$$u(t) = -Gx(t) \quad (15)$$

where G=Gain Matrix Specifying Closed Loop Pole Locations.

Together the state estimator provided by equation 13 and the gains calculated by the LQO determine the state-space controller $G_{SS}$.

Figure 8A:
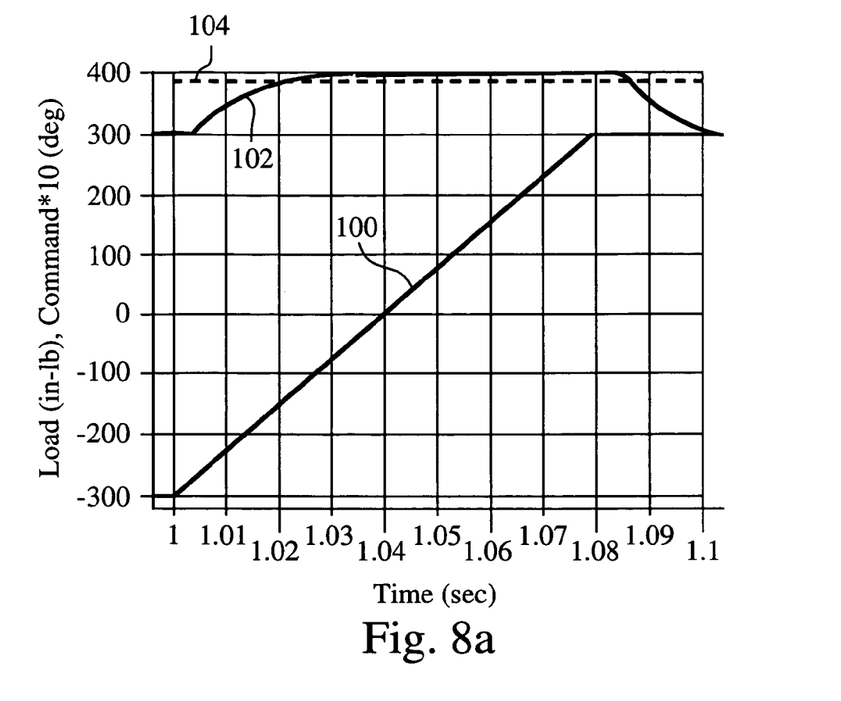
FIGS. 8a and 8b are plots of a torque-at-rate and a non-linear dynamic load, respectively.
Figure 8B:
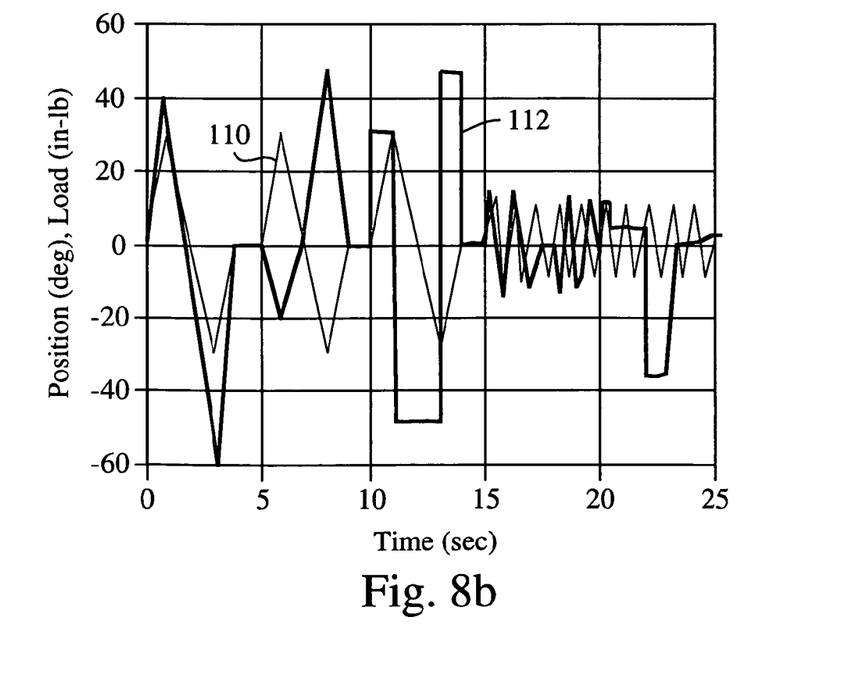

As shown in FIGS. 8a and 8b, by allowing the free end of the torsion bar to rotate independent of the rotation of the UUT in response to the DLF motor, the DLF can perform torque-at-rate and nonlinear load tests.

As shown in FIG. 8a, the application of a position command $U_{UUT}(s)$ 100 to the DLF created a constant load (torque) 102 that closely approximates a desired load command $U_{DLF}(s)$ 104. In this particular example the UUT was a G400 Series MOOG Brushless Servomotor. The state space controller for the UUT used a $3^{rd}$ order observer with tuned optimization gains to produce a 55 Hz bandwidth and commanded slews limited to 750°/sec. The UUT achieved 750°/sec for a 60° step. For 40° of the slew a constant load of ~400 in-lb±2% of the steady state load during the slewing region was achieved.

As shown in FIG. 8b, the DLF is designed to produce a variety of loads 110 through the application of command signal 112 to deal with any number of test scenarios, whether they be standardized acceptance tests, engineering investigations or actual real time flight duty cycles. From time 0 to 2 seconds it is seen that if desired the DLF can behave as a fixed end torsion bar, having a linear, proportional response to the UUT position. Time frame 2 to 4 demonstrates that the DLF can behave as the fixed end torsion bar, but unlike the torsion bar can change almost instantaneously during a test the constant at which load is proportional to UUT position. Time frame 5 to 10 seconds demonstrates that the sign of load can be changed so that it is aiding or opposing at the whim of the DLF operator. Time frame 10 to 15 seconds demonstrates that a constant load can be applied at will and can be changed mid test. Time frame 15 to 20 seconds demonstrates the DLF capability in frequency content situations. 1 Hz is used for visual purposes but higher frequencies are also applicable, limited only by the physical dynamics of the particular DLF system. 18 to 20 seconds demonstrates the ability to produce aiding loads, 17 to 18 seconds demonstrates the ability to produce no load and 18 to 20 seconds demonstrates the ability to perform like a fixed end torsion bar load providing opposing load to the UUT motion. The 20 to 25 second section is included to demonstrate that any combination of loads and UUT positions can be theoretically achieved. For this segment the UUT is moving in a 1 HZ sign wave while the load is oscillating at 10 Hz at different load levels.

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

We claim:

1. A dynamic load fixture (DLF) comprising:
   A test motor having a drive shaft;
   a torsion bar adapted for mechanical coupling to the drive shaft along an axis of rotation,
   a DLF motor for applying torque to the torsion bar to apply a load to the, drive shaft, and
   a controller for generating a command signal C(s) to the DLF motor to adjust the application of torque to the torsion bar so that the load applied to the drive shaft approximates a load command $U_{DLF}(S)$.

2. The DLF of claim 1, wherein the drive shaft has a range of motion of less than 10 turns.

3. The DLF of claim 2, wherein the drive shaft has a range of motion of less than 1 turns and a response bandwidth of greater than 10 Hz.

4. The DLF of claim 1, wherein the torsion bar has a first end that is mechanically coupled to the drive shaft and a second end that is free to rotate.

5. The DLF of claim 4, wherein the DLF motor applies torque to the torsion bar so that the load applied to the drive shaft is independent of the angular rotation of the drive shaft.

6. The DLF of claim 5, wherein the DLF motor applies torque to the torsion bar to produce a load on the drive shaft of an approximately constant torque at a given rate of rotation.

7. The DLF of claim 5, wherein the DLF motor applies torque to the torsion bar to produce a load on the drive shaft of a non-linear torque.

8. A dynamic load fixture (DLF) for testing a unit under test (UUT) having a rotating shaft, comprising:
   A torsion bar adapted for mechanical coupling to the UUT's rotating shaft along an axis of rotation;
   A motor for applying torque to the torsion bar to supply a load to the UUT;
   at least one sensor for measuring torque applied to the UUT; and
   a controller receiving as inputs a load command $U_{DLF}(s)$ and the torque applied to the UUT and generating a command signal C(s) to the motor to adjust the application of torque to the torsion bar so that the applied load approximates the load command $U_{DLF}(s)$.

9. The DLF of claim 8, wherein the controller incorporates a priori knowledge of the UUT and DLF to anticipate and correct any errors in the load caused by the response of the UUT.

10. The DLF of claim 8, wherein the controller incorporates a priori knowledge of the DLF to anticipate and correct any errors in the load caused by the response of the DLF.

11. The DLF of claim 8, wherein the controller is a state space controller $G_{ss}$ and the DLF and UUT are represented by a system of equations, comprising:
    a state estimator that uses a model of the DLF and measurements of certain output states O(s) to estimate unmeasured state variables; and
    a linear quadratic optimizer (LQO) that multiplies the measured and unmeasured states by gain coefficients and sums them together to create a feedback signal $E_{Feedback}(S)$ that is subtracted from the load command $U_{DLF}(S)$ to produce the command signal C(s).

12. The DLF of claim 8, wherein the torsion bar has a first end that is mechanically coupled to the UUT shaft and a second end that is free to rotate, said controller generating command signal C(s) whereby the load is independent of the angular rotation of UUT.

13. The DLF of claim 11, wherein the state estimator also includes a model of the UUT and receives as input a position command $U_{UUT}(s)$ to further estimate the unmeasured state variables so that the LQO generates the feedback signal $E_{Feedback}(s)$ that anticipates and corrects errors in the load caused by the response of the UUT to the load.

14. The DLF of claim 8, wherein the DLF and UUT are represented by a system of equations defining a set of open and closed loop poles, the controller comprising a feed forward controller $G_{FF}$ that anticipates and corrects errors in the load caused by the response of the UUT to the load by making an a priori correction to the load command $U_{DLF}(S)$ and a controller $G_C$ that passes the corrected load command $U_{DLF}(s)$ through a filter to generate command signal C(s), said controller $G_C$ placing the closed loop poles of the filter so that the applied load approximates the load command $U_{DLF}(s)$.

15. The DLF of claim 14, wherein the feed forward controller $G_{FF}$ incorporates a priori knowledge of the UUT and receives as input a position command $U_{UUT}(s)$.

16. A dynamic load fixture (DLF) for a rotary mechanical system, comprising:
   a unit under test (UUT) having a rotating shaft;
   a torsion bar mechanical coupled to the rotating shaft along an axis of rotation;
   a motor for applying torque to the torsion bar to apply a load to the UUT; and
   a controller incorporating a priori knowledge of the DLF and UUT and receiving as inputs a load command $U_{DLF}(s)$ and a measure of the load to generate a command signal C(s) that adjusts the load to approximate the load command.

17. The DLF of claim 16, wherein the controller is a state space controller $G_{SS}$ and the DLF and UUT are represented by a system of equations, comprising:
   a state estimator that uses a model of the DLF and measurements of certain output states O(s) to estimate unmeasured state variables; and
   a linear quadratic optimizer (LQO) that multiplies the measured and unmeasured states by gain coefficients and sums them together to create a feedback signal $E_{Feedback}(s)$ that is subtracted from the load command $U_{DLF}(s)$ to produce the command signal C(s).

18. The DLF of claim 16, wherein the controller comprises a feed forward controller $G_{FF}$ that anticipates and corrects errors in the load caused by the response of the UUT to the load by making an a priori correction to the load command $U_{DLF}(s)$ and a controller $G_C$ that passes the corrected load command $U_{DLF}(s)$ through a filter to generate command signal C(s).

19. A dynamic load fixture (DLF) for testing a unit under test (UUT) having a rotating shaft, comprising:
   a load that is mechanically coupled to the shaft; and
   a state space controller $G_{SS}$ including a state estimator that uses a model of the DLF defining a number of open and closed loop poles and measurements of certain states to estimate unmeasured state variables and a linear quadratic optimizer (LQO) that multiplies the measured and unmeasured states by gain coefficients, sums them together, and subtracts the product from a load command $U_{DLF}(s)$ to generate a command signal C(s) that controls the application of the load to the UUT's shaft, said command signal C(s) placing the closed loop poles so that the applied load approximates the load command $U_{DLF}(s)$.

20. The DLF of claim 19, wherein the LQO places the closed loop poles so that they are stable and at least as fast as the open loop poles of the model.

21. The DLF of claim 19, wherein the state estimator also includes a model of the UUT and receives as input a position command $U_{UUT}(s)$ to estimate the unmeasured state variables so that the LQO adjusts the command signal C(s) to anticipate and correct errors in the load caused by the response of the UUT to the load.

22. A dynamic load fixture (DLF) for testing a unit under test (UUT) having a rotating shaft, comprising:
   a load that is mechanically coupled to the shaft; and
   a feed forward controller $G_{FF}$ that anticpates and corrects errors in the load caused by the response of the UUT to the load by making an a priori correction to a load command $U_{DLF}(s)$; and
   a controller $G_C$ that passes the corrected load command through a filter to generate a command signal C(s) that controls the load applied to the shaft, said filter having closed loop poles that are placed so thay the applied load approximates the load command.

23. The DLF of claim 22, wherein the feed forward controller $G_{FF}$ incorporates a priori knowledge of the UUT and receives as input a position command $U_{UUT}(s)$.

24. The DLF of claim 1, wherein the controller passes the command signal C(s) through a filter based on models of said DLF and UUT to anticipate and correct errors in the applied load due to response of said DLF and UUT to load.

25. The DLF of claim 24, further comprising at least one sensor for feeding back the applied load to the controller to adjust the command signal C(s).

26. The DLF of claim 12, wherein the controller generates command signal C(s) to apply a load of an approximately constant torque at a given rate of rotation.

27. The DLF of claim 12, wherein the controller generates command signal C(s) to apply a load of non-linear torque.

* * * * *